(12) United States Patent
Smith

(10) Patent No.: US 6,936,021 B1
(45) Date of Patent: Aug. 30, 2005

(54) COMPRESSION GARMENT FOR DORSOCERVICAL SURGERIES

(76) Inventor: Veronica C. Smith, 980 Marina Way South, Richmond, CA (US) 94804

( * ) Notice: Subject to any disclaimer, the term of this patent is extended or adjusted under 35 U.S.C. 154(b) by 63 days.

(21) Appl. No.: 10/914,556

(22) Filed: Aug. 9, 2004

(51) Int. Cl.⁷ .............................................. A61F 5/00
(52) U.S. Cl. .............................. 602/19; 602/61; 2/114
(58) Field of Search .............................. 602/19, 60–79; 2/114, 102, 104, 111, 80, 247, 267, 92, 115; 128/846, 874, 888

(56) References Cited

U.S. PATENT DOCUMENTS

| | | | | |
|---|---|---|---|---|
| 3,856,004 | A | * | 12/1974 | Cox ............................ 602/19 |
| 3,968,803 | A | * | 7/1976 | Hyman ........................ 602/79 |
| 5,007,412 | A | * | 4/1991 | DeWall ....................... 602/19 |
| 5,094,648 | A | * | 3/1992 | Turner ........................ 450/155 |
| 5,095,894 | A | * | 3/1992 | Marble ........................ 602/20 |
| 5,152,741 | A | * | 10/1992 | Farnio ......................... 602/79 |
| 5,158,541 | A | * | 10/1992 | McCurley .................... 602/79 |
| 5,274,851 | A | * | 1/1994 | Simpkins et al. ............. 2/102 |
| 5,305,471 | A | * | 4/1994 | Steele et al. .................... 2/102 |
| 5,395,306 | A | * | 3/1995 | Bauerfeind et al. ........... 602/61 |
| 5,429,593 | A | * | 7/1995 | Matory ........................ 602/79 |
| 5,628,725 | A | * | 5/1997 | Ostergard ..................... 602/62 |
| 5,754,982 | A | * | 5/1998 | Gainer ............................ 2/2.5 |
| 5,945,681 | A | * | 8/1999 | Tokiguchi et al. ...... 250/492.21 |
| 5,968,003 | A | * | 10/1999 | Sisson .......................... 602/75 |
| 6,086,551 | A | * | 7/2000 | Allen ........................... 602/19 |
| 6,120,213 | A | * | 9/2000 | Stinton ....................... 405/186 |
| 6,195,802 | B1 | * | 3/2001 | Armellino ...................... 2/102 |
| 6,296,618 | B1 | * | 10/2001 | Gaber .......................... 602/75 |
| 6,364,851 | B1 | * | 4/2002 | Nafpliotis .................... 602/19 |
| 6,446,273 | B1 | * | 9/2002 | Gillen et al. ................... 2/455 |
| 6,485,446 | B1 | * | 11/2002 | Brother et al. ............... 602/20 |
| 6,533,971 | B1 | * | 3/2003 | Stess et al. ................ 264/40.1 |
| 6,557,176 | B2 | * | 5/2003 | Franco-Sion ................... 2/102 |
| 6,700,031 | B1 | * | 3/2004 | Hahn .......................... 602/41 |
| 6,834,396 | B2 | * | 12/2004 | Franco-Sion ................... 2/102 |

* cited by examiner

*Primary Examiner*—Henry Bennett
*Assistant Examiner*—Shumaya B. Ali
(74) *Attorney, Agent, or Firm*—David E. Newhouse

(57) ABSTRACT

A close-fitting, compression garment is described for providing adjustable compressive force over a surgical site in the dorsocervical region of the human body below the neck, above and between the shoulder blades of the upper back. The vest body portion of the invented garment has graduated or increasing elasticity encircling the upper torso and shoulder region of the body. Wide adjustable elastic pressure bands pressure anchored at the dorsocervical apex at the back of the vest stretch over the shoulders of the patient and adjustably anchored to anchor strips secured to the front chest surface of the vest for establishing compression over a surgical site in the dorsocervical region during recovery as needed both for rehabilitation and comfort.

8 Claims, 3 Drawing Sheets

COMPRESSION GARMENT FOR DORSOCERVICAL SURGERIES

RELATED APPLICATIONS

None.

FIELD OF THE INVENTION

The present invention relates generally to post-surgical rehabilitation garments, and more particularly, to a compression garment for post-surgical rehabilitation of patients undergoing a dorsocervical lipectomy.

BACKGROUND OF THE INVENTION

"Buffalo or dowager's hump" is an accumulation of fat on the upper back below the neck above and between the shoulder blades. This condition can occur with over secretion of cortisone by the adrenal gland, a condition called Cushing's syndrome. It is also a relatively common side effect of HIV and AIDS medications on many male patients. A dorsocervical lipectomy is a medical procedure to remove the fatty tissues forming the hump on the necks or upper backs of such patients. As with most lipectomy surgeries, post-surgical compression of the surgical site is desirable to mitigate swelling, and stretching of skin tissue due to fluid accumulation in the region under the skin where the fatty tissues have been removed.

Compression Therapy:

The application of sustained graduated compression is a key element in the treatment of all types of wounds, lipectomy surgical sites and ulcers caused by damaged or incompetent veins in the lower leg, etc. Compression hosiery is commonly used for wounds/ulcerations, located on a patient limb. Also, Elastic bands are typically fastened around encircling the torso of patients for compressing wound and surgical sites on the torso amenable to wrapping. For all other sites elastic bandages and multi-layer bandaging systems remain the principal mechanisms for effecting compression at a wound/surgery site.

Compression girdles are also used after liposuction procedures to help the skin at a surgical site reattach to the lower dermal layer. Doctors have used different types of compression wear for many years to help reshape patient body contours after sub-dermal intervention. Such garments are necessary because a human body naturally heals itself by swelling. Unfortunately, swelling can cause the improper reattachment of the skin to its new contours. Swelling can also break or dislocate wound healing tapes, sutures, staples or other devices.

The degree of compressive pressure required to optimize wound healing is a matter of some debate. The effectiveness of compression bandaging depends upon pressure provided and, this in turn, is determined by a number of factors including the physical and elastomeric properties of the fabric, the size and shape of the site, the skill or technique of the doctor/medical person applying the bandage and, most importantly, tension of the bandaging fabric post application.

Unlike stockings or tubular bandages, where the relationship between extension (a function of site diameter) and fabric tension is 'pre-programmed' into the product during the manufacturing process, the tension developed in most flat bandages during application is determined entirely by the person doing the bandaging. Studies have shown that the tension of bandages can vary significantly depending on the experience and skill of the person doing the bandaging. However, the tension achieved by an individual repeatedly performing a particular bandaging procedure can be quite consistent. Tension establishing applied pressures at the wound/surgery site often determines of the effectiveness of the treatment. If the pressure achieved is too low, the compression may be ineffective to prevent swelling and stretching. But if the pressure is excessively high there is a real possibility the resulting compression can damage tissue and cause necrosis over vulnerable areas.

Historically, attempts have been made to reduce the effects of bandaging variability by marking bandages with geometrical shapes that change from oblongs to squares when a particular level of extension (and therefore tension) has been applied to the fabric. This approach has been shown to significantly reduce variability and produce more consistent levels of compression.

Changes in Tension and Bandage Characteristics:

The use of application guides, however, fails to address a second problem associated with the use of extensible bandages, specifically the effect of changes of surface configuration of the bandaged area over time resulting in extension/ contraction of the bandage and therefore changes in compression. The physical characteristics (elasticity) of the bandage fabric and its interaction with the underlying tissue surface (e.g. degree of adhesion) also can be very important in determining tension, and therefore applied pressure.

Elastomeric materials subjected to a sustained tensioning forces also gradually relax or yield over time, typically by 10–20% over a 24-hour period. Although most yield occurs in the first couple of hours, the process does continues thereafter, though at a slower rate. This process is termed 'decay' and is a problem with elastic compression bandages where the object is a high levels of compression in-situ over an extended period. In such bandaging schemes, to deliver a specific level of pressure after three days' post application will have to be applied with higher initial tension to allow for such 'decay'.

Bandages that do not contain a significant amount of elastomer, but which rely upon heavily twisted textile yarns to provide a degree of elasticity, also exhibit decay and produce extensibility curves that show a very rapid change in tension for relatively small changes in extension. Bandages containing significant quantities of an elastomer perform much better in this respect. Elastomer containing are also better able to maintain applied tension, and 'follow-in' as the covered surface configuration shrinks while maintaining compression.

U.S. Pat. No. 6,296,618 to Gaber describes a pre/post surgical garment employing a flexible fabric fastening device. The garment provides an overall adjustable compression to specific parts of a patient's body covered by the garment. It also holds medically placed absorbent pads in desired locations and helps keep surgical sites sanitary.

U.S. Pat. No. 6,109,267 to Shaw et al. describes a therapeutic compression garment made of a unitary piece of flexible, foldable, light weight, Velcro-type hook-loop fabric. This compression garment is designed mainly for the leg and foot body parts.

There are other compression garments available in the market for post-surgical recovery purposes. However, most have just been manufactured of a simple single ply fabric-construction that fails to provide necessary compression to hold the skin in a desired position over sub-dermal surfaces.

SUMMARY OF THE INVENTION AND ADVANTAGES

The invented close-fitting, compression garment has a pair of wide, elastic compression bands for providing specific adjustable compressive force over a patients dorsocervical region and is particularly adapted to compress lipectomy surgical sites in that region of the human body. The vest body portion of the invented garment has graduated or increasing elasticity encircling the upper torso and shoulder region of a patient. Each wide, elastic compression band has one end permanently anchored at the apex of its dorsocervical section on the back to the vest on the, and stretches over the adjacent shoulder of the patient where it free end is adjustably anchored to an anchor strip secured to the front chest surface of the vest. This configuration allows the patient as well as the practitioner to easily adjust the compression needed over a surgical site in the dorsocervical region during recovery both for comfort and enhancing rehabilitation.

An object and advantage of the invented compression garment is to provide a close fitting elastic garment, that provides specific adjustable compression over a surgical lipectomy site located in the dorsocervical region of the human body below the neck, above and between the shoulder blades of the upper back.

Another object and advantage of the invented compression garment is that it that complies to contours of a surgical site, such as a dorsocervical lipectomy using adjustable elastic bands to accommodate combination of comfort and compression, and further facilitating ease of donning or removing the garment.

The advantage of multiple layers of sturdy power net material of the invented compression garment is an increasing elasticity around the upper torso shoulder region of the human body that provides adequate surface pressure in the region to hold skin tissues in a desired position over a sub-dermal "lipectomy" surgical site in the dorsocervical region over a period of time. The invented vest also includes a lower waist band to prevent "riding up" and ensure comfort to patients over prolonged periods post surgery.

It is another object and advantage of the present invention to help maintain surgical dressings in place until removed.

The following is a list of the advantages of the present invention:

1. Stops fluid build up in a sub-dermal surgical lipectomy area.
2. Gives necessary compression for promoting and assuring proper skin adhesion.
3. Adjusts compression as swelling increases or decreases to maintain constant comfort.
4. Controls swelling.
5. Helps skin better fit its new contours.
6. Is snug and composed predominantly of elastic materials for comfort as it must be worn for several weeks post surgery.
7. Easy to don adjust and remove during the healing process.
8. Maintains surgical dressings in place until removed.

DETAILED DESCRIPTION OF THE PREFERRED EMBODIMENT

Figure 1A:
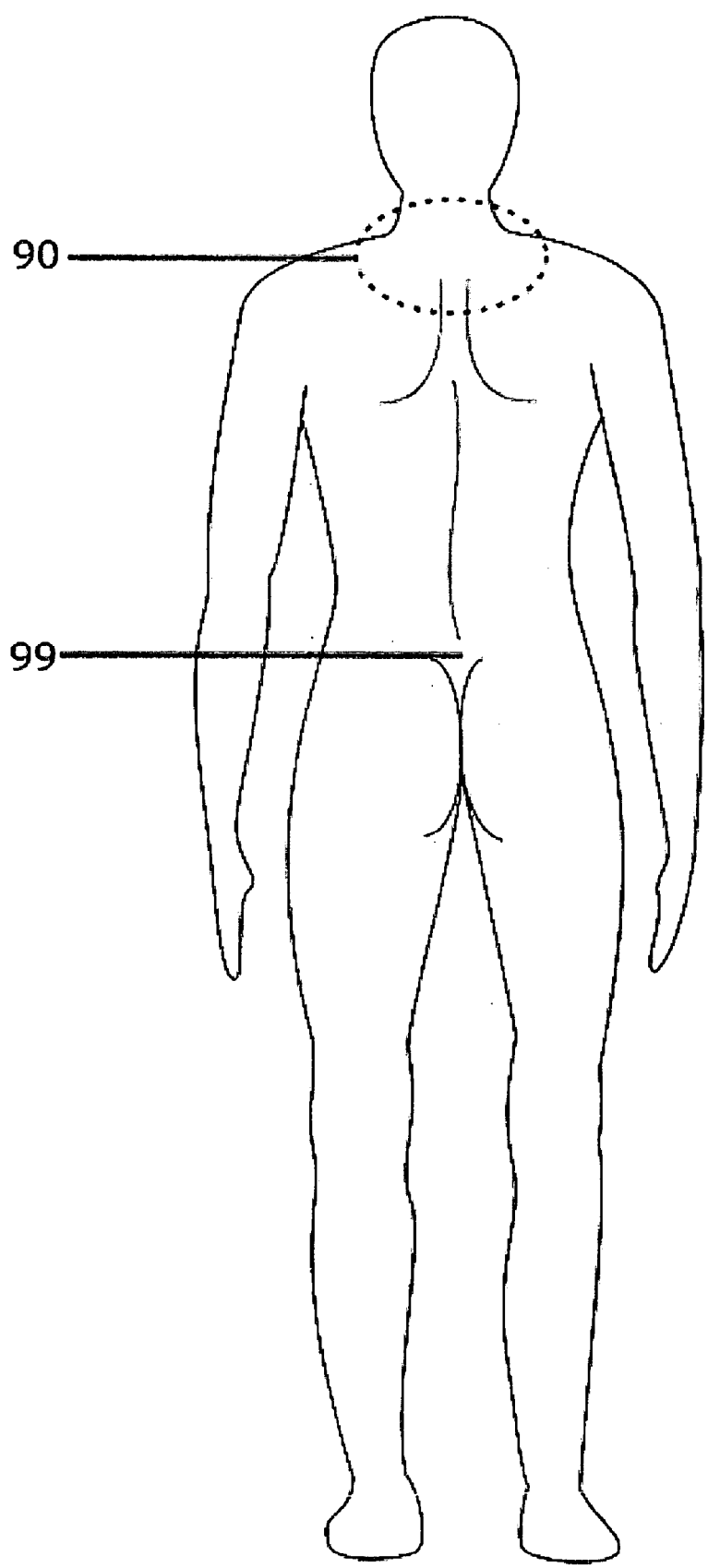
FIG. 1 is a representative drawing showing the dorsocervical region of a typical patient.
Figure 2A:
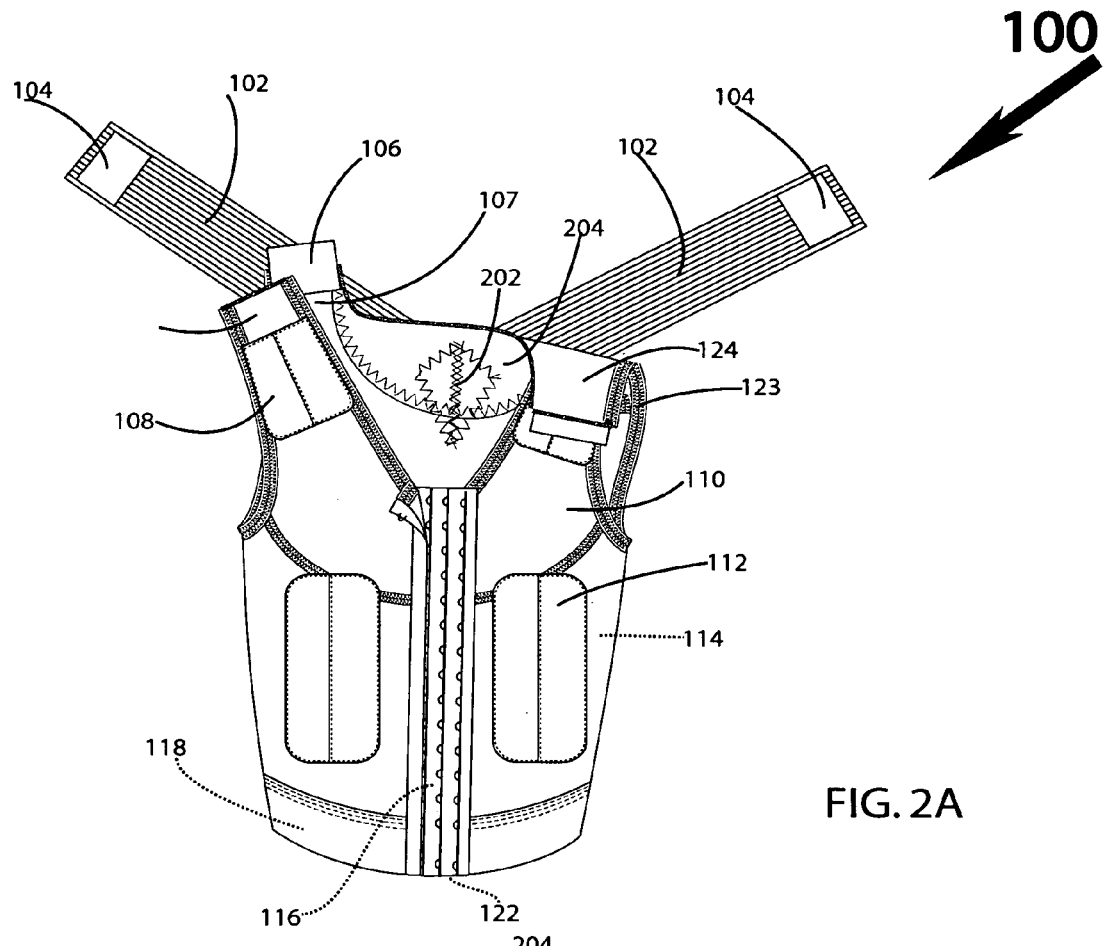
FIG. 2A is a representative front view of a preferred embodiment of a compression garment of the present invention in an opened position.
Figure 2B:
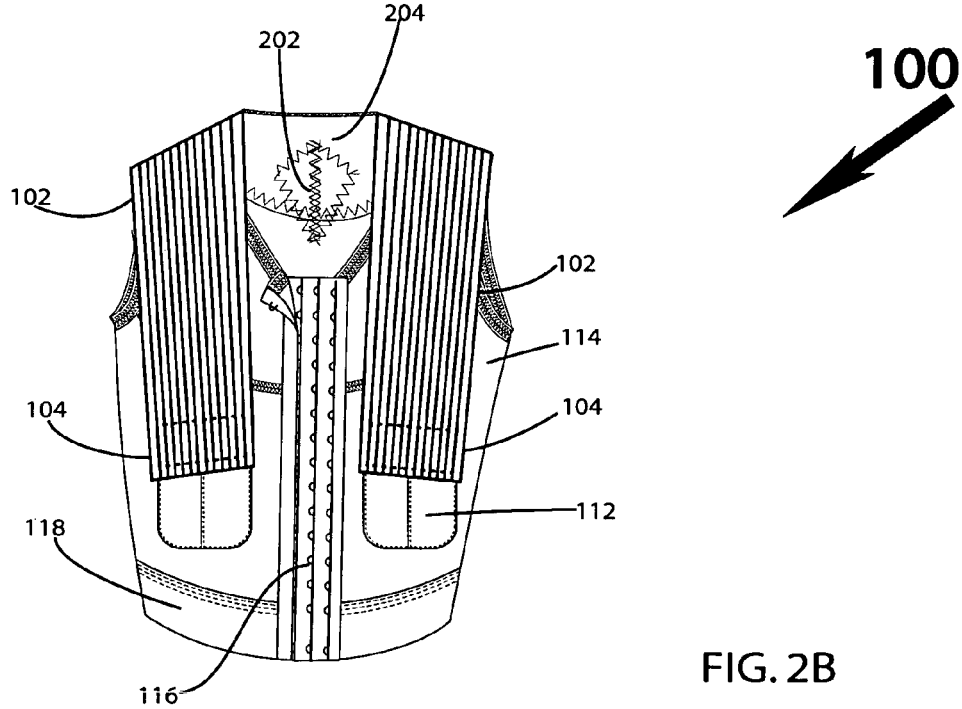
FIG. 2B is a representative front view of a preferred embodiment of a compression garment of the present invention in a closed position.
Figure 3A:
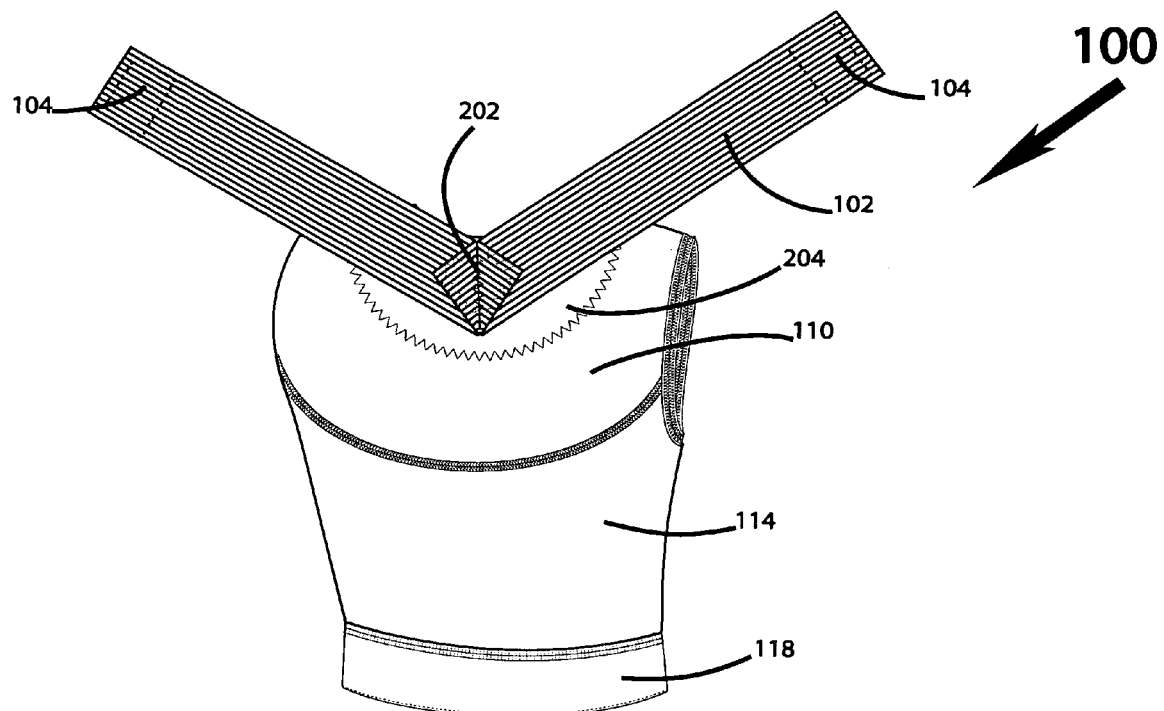
FIG. 3A is a representative back view of a preferred embodiment of a compression garment of the present invention in an opened position.
Figure 3B:
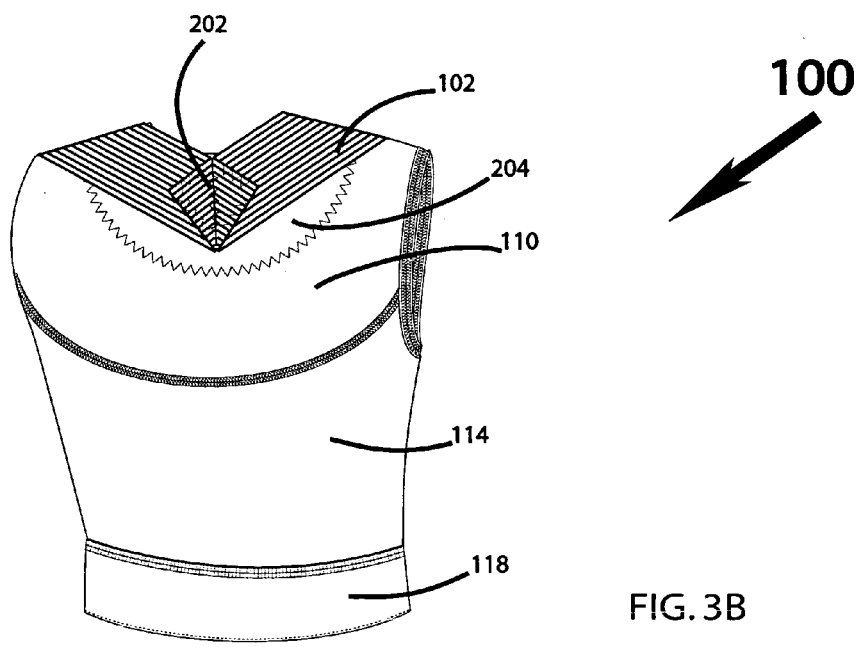
FIG. 3B is a representative back view of a preferred embodiment of a compression garment of the present invention in a closed position.

As shown in FIG. 1 the dorsocervical region 90 of a patient 99 is the area of the upper back immediately below the neck, between and above the patient's shoulder blades. Generally, the dorsocervical region is about 7.5 inches wide, and about 8 inches long. Typically, a "Buffalo" or "Dowagers" hump of fatty tissue can rise to about 2 inches in height or elevation in the dorsocervical region. It will be understood that the location, dimensions and physiognomy of patients varies. Therefore, the foregoing dimensions and locations are provided as examples only, and should in no way be deemed to limit the scope of the present invention as described.

Looking at FIGS. 2A, 2B, 3A and 3B the invented compression garment 100 is generally designed as a vest to snugly fit around about the torso and shoulder region of a patient 99. A uni-directional elastic waist band 118 encircles the patient's waist to anchor the garment 100, preventing it from riding up the patient's lower trunk. Like a vest, the invented garment fastens and opens in the front using a conventional hook-and-eye fastener array 116, i.e., vertical row, respectively of hooks 121 and one or more vertical rows of eyes 122, each sewn or incorporated into an inelastic edge seam adapted for joining left and right front sections of the garment together.

The invented garment 100 has three sections, and three layers: (i) the torso section 114 composed a single layer of a sturdy elastic, power net material, i.e., a bidirectional 'stretchy' material such as nylon spandex which yields slightly, elastically, in all directions in the fabric plane secured to the waist band 118 snugly encircling the patient's lower torso beneath his arm pits, (ii) the shoulder harness section 110 adding a second layer of a sturdy elastic, power net material tightly encircling the patient's shoulder region, and (iii) the dorsocervical section 204 located over for compressing the patient's dosocervical region adding a third layer of the sturdy elastic, power net material below the neckline.

The double layer shoulder harness section 110 is framed by a stronger, unidirectional elastic, reinforcing seam material 123 that elastically yields slightly only longitudinally in the direction of the seam, and includes shoulder straps 124 adjustably fastened together by Velcro® hook and loop fastener patches 106 and 108, respectively, allowing the wearer to establish and adjust the vertical position of the anchoring waist band 118 around his waist.

A pair of wide, unidirectional elastic, plush pile, fabric adjusting bands 102 that only stretch (allow elastic strain) longitudinally along the length of elastic adjusting band, but remains rigid across the width of the band are fastened at the apex or centerline of the dorsocervical section 204 of the invented garment 100. In particular, looking at FIGS. 3A & 3B, one end of each band 102 is sewn to the dorsocervical section 204, folded back on itself at corner at an angle of approximately 30° and to the similarly sewn folded back end of the other band 102 such that the bands extend in a 'V' from the centerline seam 202 subtending an angle of approximately 120°. The respective seams securing the folded back ends of adjusting bands 102 of invented garment define a diamond shape symmetrically bisected by a back centerline (not indicated) of the garment 100. The fee ends of the adjusting bands each have a hook Velcro® patch 104 so that the bands 102 can be stretched over the adjacent shoulder of the patient 99 and adjustably anchored to strips of Velcro® loop or pile material 112 sewn to the front surface of the torso section 114. (See FIGS. 2B & 3B.)

In particular, the compression at the apex and surrounding area of the dorsocervical region is adjusted by the varying the anchor position of the hook Velcro® patches 104 at the ends of the adjusting bands 102 on the strips of Velcro® loop or pile material 112 sewn to the front surface of the torso section 114 of the invented garment 100.

Both for reasons of health and comfort, the wide, unidirectional elastic, plush pile, fabric adjusting bands 102 of the invented garment 100 should not be constructed from conventional, tightly woven, unidirectional elastic textile material, but rather a breathable unidirectional elastic, textile material that allows air circulation and cooling vaporization of perspiration. (See for example, U.S. Pat. No. 4,344,999, D. J. Gohlke; U.S. Pat. No. 5,695,868, A. L. McCormack and related art.)

An example of a suitable unidirectional elastic, textile material for the adjusting bands 102 of the invented garment 100 would be a plurality of spaced apart parallel, spandex (elastane) plush pile fiber strips woven/bonded onto an array of transversely oriented, closely spaced, nylon monofilaments to form a band. A producer of such spandex fiber (elastane) is Dupont® Textiles and Interiors.

As described in the art, spandex fiber (elastane) is a polymer chain that is a segmented block copolymer containing long, randomly coiled, liquid, soft segments that move to a more linear, lower entropy, structure. The hard segments act as "virtual cross-links" that tie all the polymer chains together into an infinite network. This network prevents the polymer chains from slipping past each other and taking on a permanent set or draw. When the stretching force is removed, the linear, low entropy, soft segments move back to the preferred randomly coiled, higher entropy state, causing the fiber to recover to its original shape and length. Such segmented block copolymer is formed in a multi-step proprietary process. It is extruded into a fiber as a monofilament threadline or for most products into a multiplicity of fine filaments that are coalesced shortly after they are formed into a single threadline.

Essentially, the elastic response of such woven/bonded spandex fiber, plush pile bands is unidirectional in the longitudinal direction of the strips. However, the skilled practitioner, should realize, that the unidirectional longitudinal elastic response of the adjustment bands 102 only means that the transverse dimension or width of the band does not significantly change (elastically) as the band stretches longitudinally around contours presented by a patient's physiognomy. However, a consequence is that the tensile force varies transversely across the stretched band as a function of that contour. This means that a skilled wound dressing designer can orient and position transverse seams securing/anchoring the at the apex of the dorsocervical section 204 of the invented garment 100 to achieve a desired distribution of forces (in combination with the other structural and elastic forming elements of the particular garment) for compressing and restraining (locating) the lipectomy surgical site in the dorsocervical region 90 of the patient.

While the principles of the invention have been made clear in the illustrated embodiment those skilled in the art can effect modifications of structure, arrangement, proportions, the described elements, materials, and components to practice the invention, and otherwise, which are particularly adapted to specific environments and operative requirements without departing from principles set forth above. The appended claims are intended to cover and embrace any and all such modifications, with the limits only of the true purview, spirit and scope of the invention.

I claim:

1. A compression garment for providing adjustable compressive force over a surgical site located in the dorsocervical region of a human being comprising, in combination,
   a vest having:
   (i) a torso section with a first layer of a bi-directional 'stretchy' material that yields slightly, elastically, in all directions in its fabric plane secured to an elastic waistband adapted to encircle the human being's waist;
   (ii) a shoulder harness section adding a second layer of the bi-directional 'stretchy' material over the first layer adapted for tightly encircling the human being's shoulder region;
   (iii) a dorsocervical section adding a third layer of the bi-directional 'stretchy' material over the first and second layers located, for compressing the human being's dorsocervical region below a neckline of the vest;
   means for securing a left and a right front section of the vest together;
   an elastic compression band secured to the dorsocervical section of the vest, having at least a left and a right free end,
   means at the free ends of the compression band for adjustably attaching to the left and right front sections of the vest, the left and right free ends of the elastic compression bands stretching from the dorsocervical region over the left and right shoulders respectively of the human being, whereby the compression over a surgical site in the dorsocervical region can be adjusted by varying the anchor positions of the free ends of the compression band on the front sections of the vest.

2. The compression garment of claim 1 wherein the shoulder harness section further includes adjustable front and back, left and right shoulder sections adapted to fastened together over the left and right shoulders of the human being for vertically adjusting the position of the elastic waistband.

3. The compression garment of claim 2 wherein the front and back shoulder sections are adjustably fastened together with hook and loop fastener strips respectively located and secured at distal ends of the front and back shoulder sections.

4. The compression garment of claim 1 or 3 wherein loop fastener strips are secured the left and right front sections of the vest and the means secured to the free ends of the compression band for adjustable attachment to the left and right front sections of the vest comprise hook fastener patches.

5. The compression garment of claim 1 or 3 wherein hook fastener strips are secured the left and right front sections of the vest, and the means at the free ends of the compression band for adjustable attachment to the left and right front sections of the vest comprise loop fastener material patches.

6. The compression garment of claim 1 or 3 wherein hook fastener strips are secured the left and right front sections of the vest, and wherein the elastic compression band comprises a wide, unidirectional elastic, plush pile, fabric having loops adapted for fastening to hook fastener strips.

7. The compression garment of claim 1 or 3 wherein the elastic compression band secured to the dorsocervical section of the vest is composed of a right section and a left section joined together each comprising a wide, unidirectional elastic, plush pile, fabric band that elastically stretches longitudinally and is relatively rigid crosswise.

8. The compression garment of claim 7 wherein one end the left section of the compression band is sewn to the dorsocervical section of the vest, folded back on itself at a corner at an angle of approximately 30° and joined with a similarly sewn folded back end of the right section of the compression band such that the bands extending from a centerline seam joining the sections together subtend an angle of approximately 120°.

* * * * *